United States Patent [19]
Tamagni

[11] Patent Number: 5,372,572
[45] Date of Patent: Dec. 13, 1994

[54] KNEE ORTHESIS APPLIANCE

[75] Inventor: Rudenz Tamagni, Vaduz, Liechtenstein

[73] Assignee: Tamagni AG, Zurich, Switzerland

[21] Appl. No.: 675,906

[22] PCT Filed: Sep. 27, 1990

[86] PCT No.: PCT/CH90/00229
§ 371 Date: Jun. 20, 1991
§ 102(e) Date: Jun. 20, 1991

[87] PCT Pub. No.: WO91/04721
PCT Pub. Date: Apr. 18, 1991

[30] Foreign Application Priority Data

Sep. 30, 1989 [CH] Switzerland .................. 3544/89-2

[51] Int. Cl.$^5$ ............................................. A61F 5/00
[52] U.S. Cl. ........................ 602/16; 264/221; 602/26; 602/8
[58] Field of Search .......... 602/16, 23, 26, 5–8; 264/154, 221, 222; 156/155, 242, 267, 307.7

[56] References Cited

U.S. PATENT DOCUMENTS

| Re. 33,621 | 6/1991 | Lamb et al. | 602/26 X |
| 3,732,578 | 5/1973 | Pollack | 264/222 X |
| 3,901,223 | 8/1975 | May | 602/26 X |
| 4,111,195 | 9/1978 | Neufeld | 602/8 |
| 4,491,128 | 1/1985 | Haschke | 602/8 X |
| 4,523,585 | 6/1985 | Lamb et al. | 602/16 |
| 4,783,293 | 11/1988 | Wellershaus et al. | 264/222 X |
| 4,791,916 | 12/1988 | Paez | 602/26 |
| 4,803,975 | 2/1989 | Meyers | 602/26 |
| 4,821,707 | 4/1989 | Audette | 602/16 |
| 4,940,044 | 7/1990 | Castillo | 602/16 |

FOREIGN PATENT DOCUMENTS

| 369978 | 2/1983 | Austria . |
| 384733 | 12/1987 | Austria . |
| 1236669 | 6/1960 | France . |
| 1348781 | 3/1974 | United Kingdom . |

OTHER PUBLICATIONS

Medizinisch-Orthopädische Technik, vol. 108, No. 6, Nov./Dec. 1988 Gentner publisher stuttgart, DE, J. Eichler: "Knieorthesen", pp. 201–212, see p. 206, paragraph 8, Vierfach-Gelenke; p. 208–209: C.T.I.-knieorthese FIGS. 13, 16.

Primary Examiner—Richard J. Apley
Assistant Examiner—Linda C. M. Dvorak
Attorney, Agent, or Firm—Wegner, Cantor, Mueller & Player

[57] ABSTRACT

The knee orthesis appliance is made of carbon-fiber composite material with an integral Menshik linkover four bar chain (21) made of titanium. It provides the knee joint with secure and reliable support. Owing to its low weight, it is extremely comfortable to wear. The angle of bend (22) can be adjusted to suit the individual as prescribed by the doctor. The shells of the appliance are made from a positive plaster cast (1), using vacuum composite production techniques. This simple process enables the appliance to be manufactured to a high standard of quality in orthopaedic workshops. The joint plates (5,6) are inserted between the individual layers of the composite. Following filling and curing, the sidepieces (16,17) only have to be riveted to the joint plates to complete the four bar chains and hence the finished appliance.

12 Claims, 4 Drawing Sheets

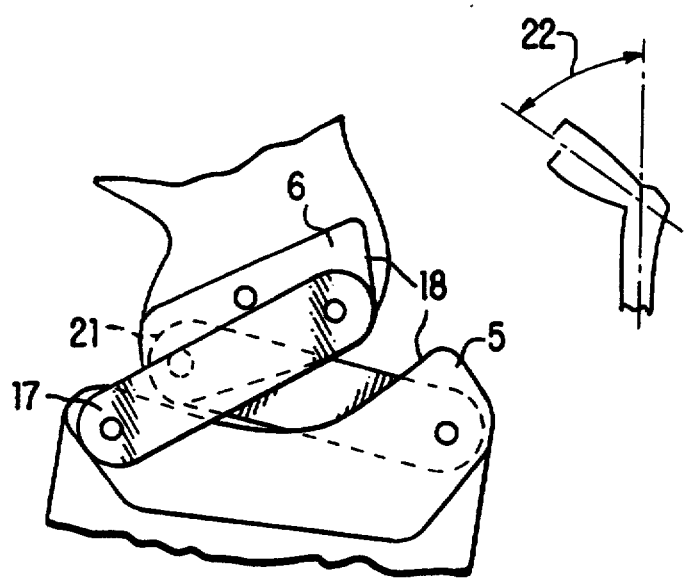
FIG. 4d
FIG. 4a
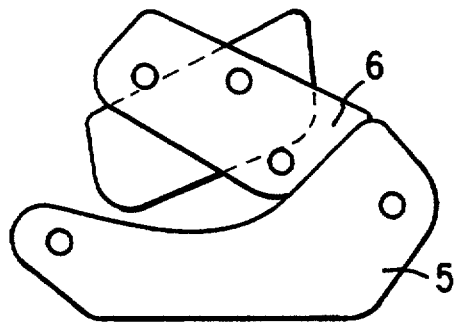
FIG. 4b
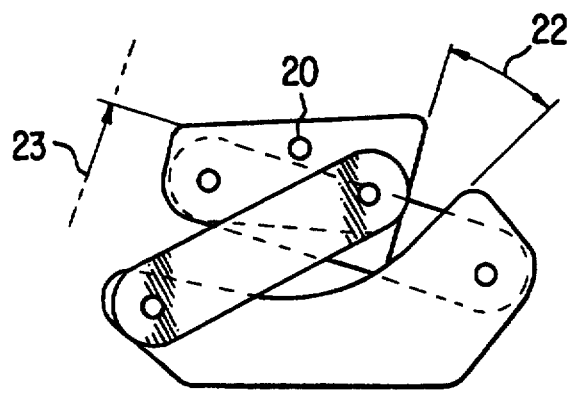
FIG. 4c

KNEE ORTHESIS APPLIANCE

BACKGROUND OF THE INVENTION

Knee orthesis appliances are used to stabilise the ligamentous apparatus in the knee.

Where knee orthesis appliances were previously prescribed mainly pre-operatively as a measure to prevent further damage to torn or overstretched ligaments and post-operatively after ligament surgery as protection, nowadays sportsmen from the most varied of disciplines use these knee splints more or less at will to protect against knee or ligament injuries.

The simplest version of the knee orthesis device has a monocentric joint; but it cannot correctly imitate the anatomical movement of the knee joint. The movement or the interplay between all elements of the knee involved in anatomical movement (joint surfaces of the femur and the tibia, cruciate ligaments, patella) is much more complex. This means that knee orthesis appliances having monocentric joints cannot move in synchrony with the thigh and the tibia. The result is annoying frictions, which reduce comfort when wearing one. Since monocentric joints are something of a temporary solution, they are not suitable for sportsmen.

The rolling/sliding movement of the knee joints which actually occurs physiologically and the particular position of the cruciate ligaments was studied and described by Menshik. The result is a so-called "linkover four bar chain" which has been named after him (hereinafter simply referred to as a four bar chain), which imitates the rolling/sliding movement very well and therefore effectively relieves the knee. However this is still far from constructing a knee splint which combines a high level of worn comfort and good management of the ligaments, preconditions which are considered to be self-evident in high performance sport today.

STATE OF THE ART

Today, ready-made splints are available for attaching to four bar chains which can be obtained separately. These knee splints are secured to the knee joint by ready to use bandages. These bandages have pockets into which the ready-made splints are inserted. However, the splints have a not inconsiderable amount of play in the pockets, therefore they move backwards and forwards, which is why the knee is badly managed in conventional splints. The security required by the ligament is therefore not available under heavy or extreme loads.

To now achieve a more exactly fitting shape, the most modern production techniques are exploited: with CAD/CAM support, knee splints can be milled out of a massive single block of carbon fibre, after measurements of the knee joint and associated parts of the femur and tibia have been taken by a laser scanner and digitised. However, knee splints manufactured in this way do not have a four bar chain and have the positive disadvantage of being very expensive due to the enormous technical expense (integrated CAD/CAM manufacturing station).

SUMMARY OF THE INVENTION

The new carbon-fiber composite layer construction knee orthesis appliances are an extremely good fit and achieve their objective in an excellent manner thanks to the Menshik four bar chain.

BRIEF DESCRIPTION OF THE DRAWINGS

FIGS. 4a, 4b, 4c and 4d show the four bar chain assembled and its method of operation;

DETAILED DESCRIPTION OF THE PREFERRED EMBODIMENTS

Its low weight (approx 360 g) and simple manufacture based on a simple positive plaster cast (1) of the knee, are excellent additional characteristics of the carbon-fiber composite material knee orthesis appliance (7) (FIG. (1)). Because a simple plaster cast (1) serves as a base, this guarantees that the carbon-fiber composite construction knee orthesis appliance (7) can be manufactured at low prices and with consistently good quality in specially equipped orthopaedic workshops.

Figure 2:
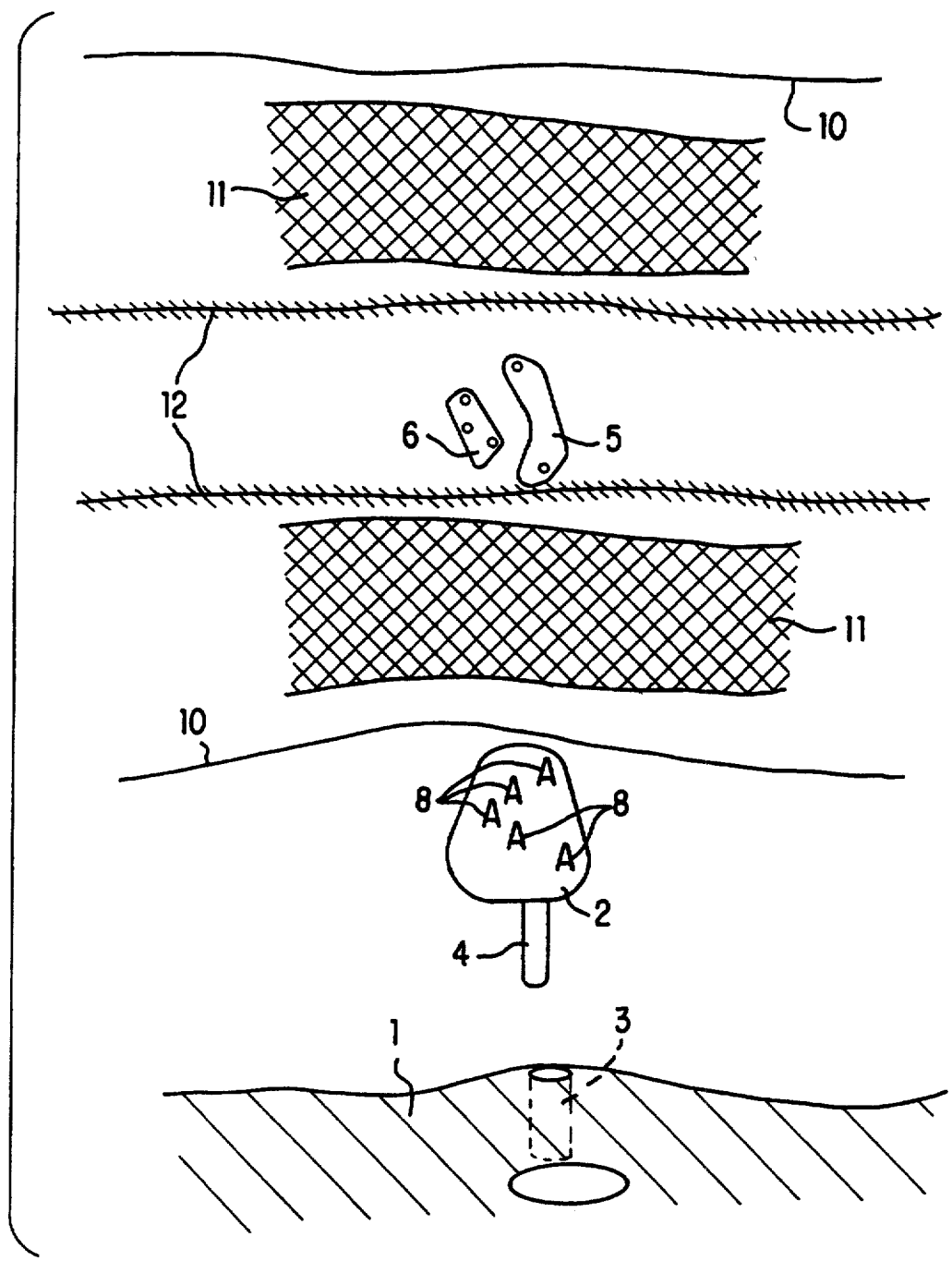
FIG. 2 shows the construction/manufacture of the knee orthesis appliance

In detail, production is as follows: firstly a negative plaster cast is made of the leg which will wear the knee splint. The knee splint will involve three-quarters of the leg. After hardening, the negative plaster cast is cut laterally and removed from the leg. It is then put together again and bound with plaster bandages. This negative mould is then filled with liquid plaster, which provides a positive plaster cast (1) as shown in FIG. 2, and we therefore achieve an exact imitation of the patient's knee joint. Any possible irregularities can then be smoothed out by subsequent modelling.

Figure 3:
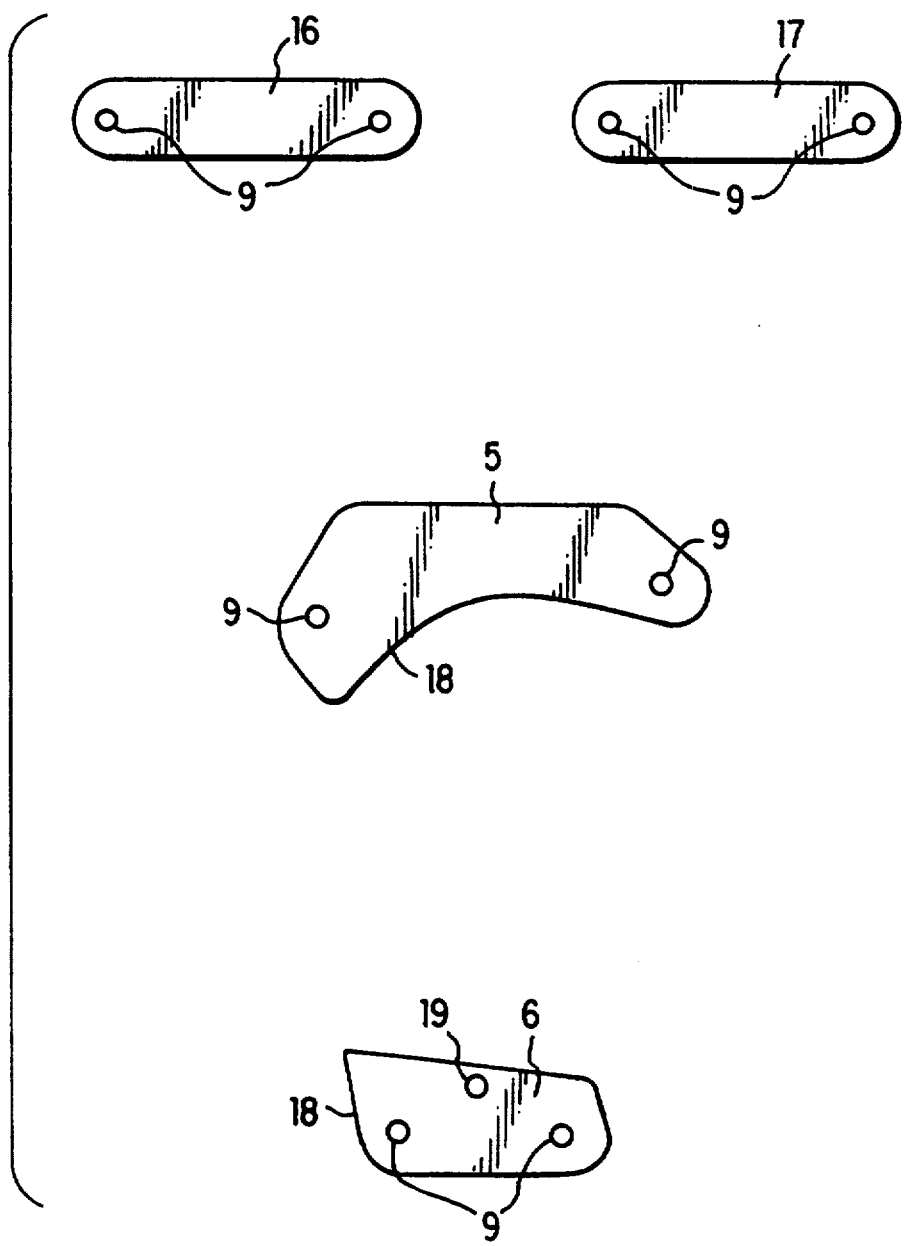
FIGS. 3a, 3b, 3c and 3d show parts of the four bar chain.

Now two basic shaping plates 2 are placed in the positive plaster cast (1) in the lateral and medial area of the knee joint, in which the four bar chains (21), shown in FIG. 4a, are to be located. To this end, two holes (3) in which the retaining pins (4) of the basic shaping plates (2) are screwed as shown in FIG. 2, are bored in the positive plaster cast. It is now decisive that in a procedure (described later), the crescent-shaped lower joint plate (5) as shown in FIG. 3 and the upper trapezoidal joint plate (6) of the four bar chain can be pre-positioned and completely integrated into the carbon-fiber composite construction knee orthesis appliance (7) itself. The four bar chains (21) which finally result are absolutely free of play and exactly positioned, which guarantees a previously unheard-of level of security for the knee joint ligamentous apparatus. It is self-evident that the level of wearer comfort is considerably increased; a highly accurate fit allows the patient to forget the knee orthesis. It should be pointed out here that the basic shaping plates 2 for positioning the joint plates (5,6) have positioning pins (8) shown in FIG. 2 whose position must match that of the boreholes (9) shown in FIG. 3 in the joint plates. The additional significance of the basic shaping plate will be dealt with later. Additionally, the hollow space necessarily created between the plaster cast (1) and the inserted basic shaping plates (2), is filled with plasticine. A knitted cotton sock (not shown in FIG. 2) must be pulled on over the positive plaster cast before we begin manufacturing the carbon-fiber composite. The knitted cotton sock is ultimately is removed at the end of the process of making the orthotic, and its sole function is to keep residual moisture in the plaster cast (1) away from the PVA (polyvinyl acetate) foil. A carbon-fiber layer (11) now follows. This is a carbon-fiber mat netting with 200 strands per square centimeter. This mat is placed axially around the plaster cast and glued together at the posterior side of the leg (that is "at the back" of the leg). Now the tubular knitted glass fiber (12) which serves to provide mechanical strength, can be pulled on. The first half of the carbon-fiber composite layer is now ready. The joint plates (5,6) shown in FIG. 2 can now be fitted on the positioning pins in the basic shaping plate (1) as discussed above. This is very easy to do, because the positioning pins penetrate well through the thin PVA foil (10), the carbon-fiber layer (11) and the knitted glass fiber (12). It is now essential for the joint plates (5,6) to be glued onto the knitted glass fiber lying below, in order that they do not subsequently move. Knitted glass fiber has the added advantage over glass fiber matting, that it does not break up into fibers when pulled. This directly increases the quality of the carbon-fiber composite since, viewed mechanically, the load-bearing mat shows no breaks, which would restrict the load-bearing capacity of the carbon-fiber composite layer.

Now the second, outer half of the carbon-fiber composite is layered, by applying a second layer of knitted glass fiber (12) as shown in FIG. 2. In order to stiffen the area of the four bar chain mechanically (to achieve the stability required for joint splint areas), glass fiber matting (not shown in FIG. 2) is wound twice crossways around the area of the joint. This is followed by a further, all-covering layer of knitted glass fiber (12). A further layer of carbon-fiber netting is laid over this, upon which a covering layer of PVA foil is laid. In summary, we then have a "composite sandwich", whose inner layers have been laid between two PVA foils around the plaster cast.

Now, a liquid laminate (resin and hardener) is poured between these foils. The rough poured mold is then connected to a vacuum and the air evacuated. Doing this presses the layered parcel firmly against the plaster cast and also completely removes the air between the layers of material; the layers of material are evenly saturated by the flowing laminate. This process is best known as the vacuum procedure and is excellently suited, according to experience, to special designs on plaster molds. It is now quite clear why, as discussed above, the hollow space between the basic shaping plates (2) and the positive plaster cast (1) are filled with plasticine. We have to prevent the inner PVA foil being torn by the evacuation of any residual air bubbles which, with the flowing laminate, would lead to the basic shaping plates also being incorporated in the orthotic. Curing in the vacuum procedure takes place at room temperature and lasts for approximately one hour. The splint mold is now ready for final working.

Figure 1:
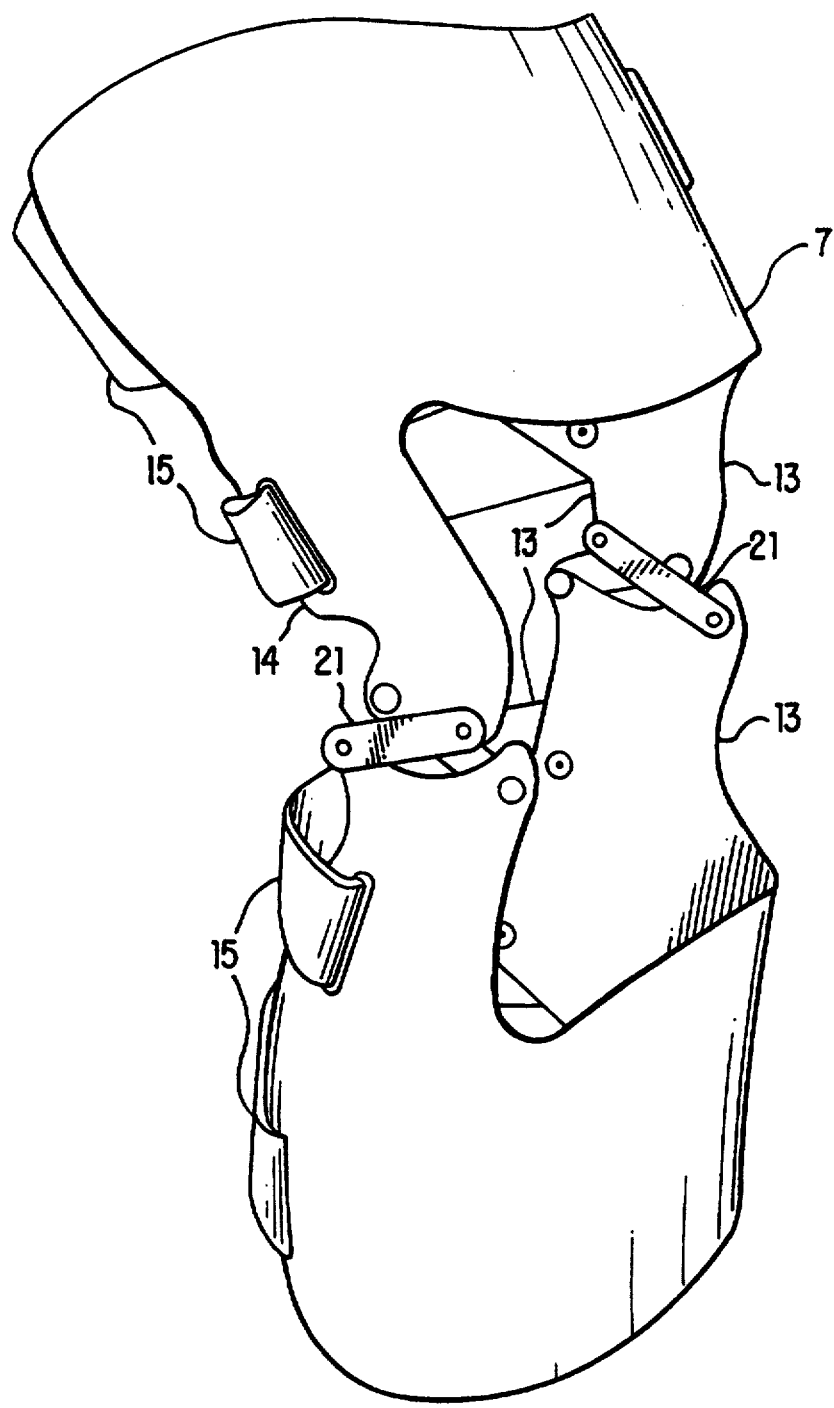
FIG. 1 shows the overall view of the knee orthesis appliance.

Firstly, the contours of the knee joint (13) is shown in FIG. 1 are cut out on the front and rear of the knee orthesis. This frees the parts of the knee which have to move. The knee orthesis can now be cut down to the final length. After this, the plaster cast is no longer required and is subsequently destroyed after the orthesis has been delivered. The (re-usable) basic shaping plates are removed. The cotton stocking and plasticine are likewise removed. The result is that we obtain the knee orthesis as a still rigid semi-finished product. The orthesis is sawn through between both joint plates (5,6), so that the upper and lower halves can be worked on independently. Now, for example, excess carbon-fiber composite material can be ground down, principally between the joint plates. Both halves are cut open along their length at the back, in order that the knee orthesis appliance can be pulled on. Slots (14) are cut for the fastenings (15) and a tibia cushion (not shown) is put in to increase wearer comfort. Finally, the inner sidepiece (16) and the outer sidepiece (17) are riveted, with the integrated joint plates, to the finished four bar chain (21) shown in FIG. 4 and, at the same time, to the finished knee orthesis appliance (7) shown in FIG. 1. The fact that the sidepieces (16,17) and the joint plates (5,6) are made of titanium, which is well-known to combine the best tensile strengths with astoundingly low weight, contributes to the low weight of approx. 360 g. Use of carbon-fiber composite material for the knee orthesis appliance also results in the lowest weight with very high strength in relation to the necessary material thickness.

We have to look more closely at the basic shaping plates (2) and the function of the four bar chain (21), shown in FIG. 4a, to see the additional advantages of the new knee orthesis. As discussed, the joint plates (5,6) are positioned thanks to the basic shaping plate (2). The mutual position of the joint plates in manufacturing the knee orthesis depends on how greatly the patient's knee can be straightened. A straightened leg with a corresponding angle of bend of 0°, which is never obtained following surgery, would be ideal. (The angle of bend (22) shown in FIG. 4d is the assumed angle between the axis of the upper femur and the assumed lengthening of the lower femur beyond the knee.) Basic shaping plates are therefore made for angles of bend of 20°, 30°, 40° and 45° at least. Basic shaping plates can, of course, be made for any angle desired. This guarantees that the joint plates (5,6) are positioned, at the time the knee splint is produced, at the present angle of bend which suits the patient for whom the plaster cast (1) was made.

Furthermore, the new knee orthesis appliance cannot be hyperextended (negative angle of bend). FIG. 4 shows that with the leg fully extended (angle of bend 0°), the straight flank (18) of the crescent-shaped lower joint plate (5) (FIG. 3) serves as a point for the flank (18) to be attached to the upper joint plates (6). In addition, the joint plates of the individual four bar chains which are opposite each other respectively, must be positioned exactly parallel and identically, in order to prevent the knee orthesis appliance from so-called opening up when bending the knee. There will be positioning tolerances despite careful manufacture; these can be very easily evened out by subsequently grinding the stop flanks (18) shown in FIG. 3. Another decisive advantage of the new knee orthesis appliance is that the angle of bend (22) can be limited in a very easy manner. This is respectively required if the surgeon orders that the patient should only bend the knee in a range between 20° and 60°. The first method of limiting the angle consists of not removing all the residues when subsequently machining the composite material between the joint plates (5,6). This automatically produces limited freedom of movement in the joint plates and therefore a limited angle of bend. Once the patient is allowed to bend the knee more strongly after a certain period, we only have to grind the composite material further down. The second method consists of inserting a stop screw (20) (cylinder head or self-tapping screw) in the holes (19) provided for this in the upper joint plates and allowing its thread to stick out so far as to serve as a stop for the inner sidepiece (14) of the four bar chain. Of course, you must ensure that the screw is prevented from unscrewing and that it cannot injure the skin of the knee. It can now be seen that the straightening movement of the knee is limited if the upper joint plate (6) moves towards the lower joint plate (5), a movement which is only possible to a certain extent due to the stop screw (20). FIG. 4c shows how the upper edge of the inner sidepiece (16) rests on the stop screw (20) when the knee is straightened in direction (23), and limits the extension angle (25), which we again find between the flanks of both joint plates. To make this more clear, FIG. 4b shows the position of the joint plates (5,6) at an angle of bend of 0° (upper joint plate pulled out) and at a selected angle of bend (upper joint plate (6) is the dotted line). The extension angle (25) and the angle of bend (22) can be adapted individually, because we only have to select the position of the holes and determine the side on which the thread should protrude. In doing so, it is self-evident that one of the two four bar chains limits the angle of bend, while the other limits the extension angle.

Patients can be released from hospital care earlier thanks to the new composite layer design knee orthesis appliance. The healing process is markedly accelerated which allows the patient to return to work more quickly. In addition, expensive follow-up treatments can be omitted, thanks to the excellent stability which the knee is given. Joint arthroses will not occur very often, with the likelihood of a subsequent, very expensive artificial knee-joint implant falling to a minimum. This will more than compensate for the costs of such a knee orthesis appliance.

The new knee orthesis appliance can also be worn without difficulty under jeans, due to the low weight and the snug-fitting shape. These advantages are also appreciated by sportsmen in all disciplines. For example, the close fitting knee orthesis appliance fits into a skier's racing suit without difficulty. Ice hockey players, rowers, tennis players, weight lifters and footballers, to name but a few, will certainly use the knee orthesis appliance as a preventive measure because it effectively protects the knee joint, fits completely and is comfortable to wear due to the low weight. The new knee orthesis appliance will replace all existing products of this nature, because it represents a truly progressive step in orthopaedic engineering due to the systematic use of the most modern materials.

REFERENCE NUMBER INDEX

1. Plaster Cast
2. Basic Shaping Plate
3. Hole
4. Retaining Pin
5. Lower Joint Plate
6. Upper Joint Plate
7. Knee Orthesis Appliance
8. Positioning Pin
9. Borehole
10. PVA foil
11. Carbon Fiber Matting Layer
12. Knitted Glass Fiber
13. Contour of Knee Orthesis Appliance
14. Slots
15. Fastening
16. Inner Sidepiece
17. Outer Sidepiece
18. Stop Flank
19. Borehole for the Stop Screw
20. Stop Screw
21. Four Bar Chain
22. Angle of Bend
23. Direction of Extension
24. Upper Edge of the Inner Sidepiece 16
25. Extension Angle

I claim:

1. A process for manufacturing a knee orthesis appliance for stabilising the ligamentous apparatus in the knee with a four bar chain, comprising: making a positive plaster cast of a leg, fixing thereon at least one basic shaping plate in a position corresponding to the lateral area of the knee joint against which a four bar chain is to rest, applying a carbon-fiber composite layer to the plaster cast and over the basic shaping plate and positioning a lower joint plate and an upper joint plate of the four bar chain on the basic shaping plate, casting the carbon-fiber composite layer with a laminate, hardening the composite and laminate, cutting out contours of the knee joint from the knee orthesis appliance and removing the plaster cast, whereby said at least one basic shaping plate is removed.

2. A process in accordance with claims 1, wherein two basic shaping plates are used.

3. A process in accordance with claim 2, wherein a basic shaping plates are fixed in the positive plaster cast with retaining pins.

4. A process in accordance with claim 1 wherein hollow space between the plaster cast and the basic shaping plate is filled with a plastic material.

5. A process in accordance with claim 1, further comprising applying an initial layer of carbon-fiber composite material to the plaster cast, fitting the lower and the upper joint plate thereon and applying a second carbon-fiber composite layer.

6. A process in accordance with claim 5, wherein the lower and the upper joint plates are located on positioning pins in the basic shaping plate, which extend through the first carbon-fiber composite layer.

7. A process in accordance with claim 5, further comprising applying a foil to the plaster cast over the basic shaping plate, after which the first carbon-fiber composite layer is applied and then the joint plates are attached to the basic shaping plate, whereafter the second carbon-fiber composite layer is applied, to which a covering layer in the form of a plastic film is applied.

8. A process in accordance with claim 7, wherein the first and second layers of the carbon-fiber composite layer are a carbon-fiber fiber net matting.

9. A process in accordance with one of the claim 7, wherein a fluid laminate is poured into the carbon-fiber composite layers between the plastic foil on the plaster cast and the covering layer.

10. A process in accordance with claim 5, wherein the lower and upper joint plates are glued onto a layer of glass fiber which is applied to the first carbon-fiber composite layer prior to the joint plates being positioned.

11. A process in accordance with claim 1 wherein at least one basic shaping plate accommodates a knee angle of bend of 0° to 60°.

12. A process according to claim 1, further comprising dividing the appliance between the joint plates such that an upper half and a lower half are created and connecting said four bar chain to said halves.

* * * * *